United States Patent [19]

Schwarze et al.

[11] 3,956,304

[45] May 11, 1976

[54] PREPARATION OF 2-METHYL-4-ISOPROPYLIDENE-2-OXAZOLIN-5-ONE

[75] Inventors: Werner Schwarze, Frankfurt; Gerd Schreyer, Grossauheim both of Germany

[73] Assignee: Deutsche Gold- und Silber-Scheideanstalt vormals Roessler, Germany

[22] Filed: Sept. 12, 1974

[21] Appl. No.: 505,607

[30] Foreign Application Priority Data

Sept. 12, 1973 Germany.............................. 2345835

[52] U.S. Cl............................................. 260/307 A
[51] Int. Cl.². ...................................... C07D 263/42
[58] Field of Search................................. 260/307 A

[56] References Cited

UNITED STATES PATENTS 2,569,801   10/1951   Cook et al. ........................... 260/307

OTHER PUBLICATIONS

Elderfield– "Heterocyclic Compounds" –Vol. 5– John Wiley Press (1957) – pp. 338–339.

Primary Examiner—Raymond V. Rush
Attorney, Agent, or Firm—Cushman, Darby & Cushman

[57] ABSTRACT

N-acetyl-DL-penicillamine is prepared from DL-valine by converting the DL-valine into 2-methyl-4-isopropylidene-2-oxazolin-5-one using chloroacetyl chloride at 50° to 150°C. and then converting the 2-methyl-4-isopropylidene-2-oxazolin-5-one into the N-acetyl-DL-penicillamine.

13 Claims, No Drawings

PREPARATION OF 2-METHYL-4-ISOPROPYLIDENE-2-OXAZOLIN-5-ONE

The invention is concerned with a process for the production of N-acetyl-DL-penicillamine from DL-valine by converting the valine into 2-methyl-4-isopropylidene-2-oxazolin-5-one using chloroacetyl chloride and converting the 2-methyl-4-isopropylidene-2-oxazolin-5-one into the N-acetyl-DL-penicillamine. N-acetyl-DL-penicillamine serves as a starting material for the recovery of DL-penicillamine.

It is known that by reacting valine with chloroacetyl chloride in aqueous alkaline medium at temperatures below 0°C. to obtain chloroacetyl valine and by reacting the chloroacetyl valine with acetic anhydride at 60°C. to form 2-methyl-4-isopropylidene-2-oxazolin-5-one and subsequently to recover the N-acetyl-penicillamine from this (The Chemistry of Penicilline, Princeton University Press, 1949, pages 464–465). The process for the production of 2-methyl-4-isopropylidene-2-oxazolin-5-one from the valine is expensive because the reaction proceeds in two steps. Besides only moderate yields, namely at most 60%, are produced.

There has now been found a process for the production of N-acetyl-DL-penicillamine from DL-valine by converting the DL-valine into 2-methyl-4-isopropylidene-2-oxazolin-5-one using chloroacetyl chloride and converting the 2-methyl-4-isopropylidene-2-oxazolin-5-one into the N-acetyl-DL-penicillamine characterized by reacting the DL-valine with the chloroacetyl chloride at temperatures between about 50° and 150°C. At these temperatures the valine is converted directly into the 2-methyl-4-isopropylidene-2-oxazolin-5-one. Surprisingly, substantially higher yields were produced than in the two step process.

To carry out the process of the invention the valine can be introduced directly into the chloroacetyl chloride. However, it is advantageous to carry out the reaction in organic solvents. As solvents there are suitably used materials which are inert to the reactants under the reaction conditions. Preferably there are used aliphatic and aromatic hydrocarbons, e.g., gasoline having boiling points between 80° and 200°C., n-heptane, n-octane, n-decane, 2,2,4-trimethylpentane, undecane, dodecane, n-hexadecane and other alkanes, cyclohexane, benzene, toluene, xylene, halo substituted hydrocarbons, especially chloro substituted hydrocarbons such as haloalkanes, e.g., carbon tetrachloride, 1,2-dichloroethane, 1,1-dichloroethane, 1,1,1-trichloroethane, 1,1,2-trichloroethane, chloropropane, chlorobenzene, o-dichlorobenzene, or ethers, e.g., alkyl ethers such as diisopropyl ether, di-n-butyl ether, ethyl n-butyl ether, di-n-propyl ether, diisoamyl ether, di-n-amyl ether or aromatic ethers such as anisole and phenetole. Advantageously the solvents added have a low water content and preferably are anhydrous.

It is suitable to use at least equivalent amounts of chloroacetyl chloride to the valine, i.e., mole for mole. Preferably there are used at least 1.8 moles, especially at least 2.0 moles of chloroacetyl chloride per mole of valine. The molar ratio of chloroacetyl chloride can be as large as one wishes, i.e., there is no upper limit. In a given case the higher the water content of the materials the more chloroacetyl chloride is necessary. In adding water free materials it can be advantageous not to exceed a molar ratio of chloroacetyl chloride to valine of 4 to 1.

The reaction takes place in a suitable manner at temperatures between about 50° and 150°C., preferably between 70° and 120°C. The pressure can range widely and is not critical. However, it is recommended in order to use simple apparatus to employ normal pressure, or if necessary moderately reduced or elevated pressures. The temperature and pressure in a given case to a certain extent are adjusted according to the type of solvent and the molar ratio of chloroacetyl chloride to valine.

Generally, it is suitable to constantly remove the hydrogen chloride which is formed in the reaction. It is advantageous for this purpose to lead inert gases such as carbon dioxide, argon or nitrogen through the reaction mixture.

By distillation under reduced pressure there is recovered from the reaction mixture a mixture of 2-methyl-4-isopropylidene-2-oxazolin-5-one and chloroacetic acid. These can be added directly for further reaction of the 2-methyl-4-isopropylidene-2-oxazoline-5-one.

The recovery of the N-acetyl-DL-penicillamine can take place in known manner, for example, according to a process set forth in the Chemistry of Penicilline, Princeton University Press, 1949, especially pages 464 to 466. The entire disclosure of The Chemistry of Penicilline pages 464 to 466 is hereby incorporated by reference. It is advantageous to first neutralize the mixture of 2-methyl-4-isopropylidene-2-oxazolin-5-one and chloroacetic acid by means of an organic base, especially a tertiary amine or base such as triethylamine, tributyl amine or N-methyl morpholine in an inert solvent, especially in a hydrocarbon (such as those set forth above, for example) or an ether (such as those set forth above, for example), or an alcohol, e.g., methyl alcohol, ethyl alcohol, isopropyl alcohol, propyl alcohol or butyl alcohol or an ester, e.g., methyl acetate, ethyl acetate, propyl acetate, methyl propionate or ethyl butyrate. Preferably, the organic solvent is miscible with water, e.g., lower alkanols are especially suitable. To the 2-methyl-4-isopropylidene-2-oxazolin-5-one which is now present as the salt there is added hydrogen sulfide, in a given case with heating, and by heating the product in the presence of water, in a given case after removal of the organic solvent, the oxazoline ring is split and the N-acetyl-DL-penicillamine thus formed is separated off by acidification.

A preferred method for the recovery of the N-acetyl-DL-penicillamine is to add the mixture of 2-methyl-4-isopropylidine-2-oxazolin-5-one and chloroacetic acid dropwise into an at least stoichiometrical amount of the tertiary organic base in a lower alkanol. Hydrogen sulfide is led into this mixture at a temperature of about 40° to 60°C., the reaction mixture, in a given case after drawing off the alcohol, diluted with water, heated to a temperature between about 50° and 100°C. and finally by acidification regulate to a pH value which corresponds to that of the N-acetyl-DL-penicillamine or is less, and thereby to separate the N-acetyl-DL-penicillamine.

Unless otherwise indicated, all parts and percentages are by weight.

EXAMPLE

A suspension of 117 grams of DL-valine (1 mole) in 500 ml of toluene were heated to 70°C. while passing nitrogen through the suspension, and in the course of 5 minutes were added 226 grams (2 moles) of chloroacetyl chloride. The mixture was subsequently held at the boiling point with reflux for 3 hours with the further passage of nitrogen. In all 3 moles of hydrogen chloride gas were driven off. The toluene was distilled off from the remaining reaction mixture at 65 to 80 millibar. The residue, a brown oil, was distilled at 0.13 millibar and a boiling temperature of 65° to 67°C. There were obtained 187 grams of a light yellow oil. As was ascertained by gas chromatography this contained 60.5 weight % of 2-methyl-4-isopropylidene-2-oxazolin-5-one and 37.9 weight % of chloroacetic acid. The yield of 2-methyl-4-isopropylidene-2-oxazolin-5-one based on the valine added was, therefore, 82%.

A portion of the mixture of 2-methyl-4-isopropylidene-2-oxazoline-5-one and chloroacetic acid was poured into water for further examination. After a short time there separated out colorless crystals having a melting point of 203° to 204°C. The substance was identified as 2-acetamido-3,3-dimethylacrylic acid. The yield was nearly quantitative.

23 grams of the mixture of 2-methyl-4-isopropylidene-2-oxazolin-5-one (0.1 mole) and chloroacetic acid were dropped into a solution of 10.5 grams of triethylamine in 100 ml of methanol. While raising the temperature of 50°C. hydrogen sulfide was led in for 2 hours. The mixture was concentrated under reduced pressure. The residue, after addition of 75 ml of water, was held for 1 hour at 96°C. The reaction mixture was then adjusted to a pH of 1 by means of hydrochloric acid. The N-acetyl-DL-penicillamine which separated after a short time was filtered under suction, washed with ice water and dried under reduced pressure. There were recovered 11.6 grams, corresponding to a yield of 60% based on the 2-methyl-4-isopropylidene-2-oxazolin-5-one added. The substance had a melting point (decomposition point) of 178°C. and a molecular weight of 191. The analysis showed (in weight percent):

|  | C | H | N | S |
|---|---|---|---|---|
| Found | 43.9 | 6.8 | 7.2 | 16.6 |
| Calculated for $C_7H_{13}O_3NS$ | 43.9 | 6.6 | 7.3 | 16.8 |

What is claimed is:

1. A process for the production of 2-methyl-4-isopropylidene-2-oxazolin-5-one in a single step comprising reacting DL-valine with chloroacetyl chloride at a temperature between about 50° and 150°C., there being employed at least 1 mole of chloroacetyl chloride per mole of valine.

2. A process according to claim 1, wherein the temperature is between 70° and 120°C.

3. A process according to claim 2, wherein the reaction is carried out in an inert organic solvent.

4. A process according to claim 3, wherein an inert gas is passed through the mixture during the reaction.

5. A process according to claim 4, wherein there are used at least 2 moles of chloroacetyl chloride per mole of valine.

6. A process according to claim 5 wherein there are used 2 to 4 moles of chloroacetyl chloride per mole of valine.

7. A process according to claim 1, wherein the reaction is carried out in an organic solvent.

8. A process according to claim 7 wherein there is employed at least 1.8 moles of chloroacetyl chloride per mole of valine.

9. A process according to claim 8 wherein there are used 1.8 to 4 moles of chloroacetyl chloride per mole of valine.

10. A process according to claim 1 wherein 1 to 4 moles of chloroacetyl chloride are employed per mole of valine.

11. A process according to claim 1 wherein the process consists essentially of reacting the DL-valine with chloroacetyl chloride at a temperature between about 50° and 150°C.

12. A process according to claim 11 wherein there are employed at least 1.8 moles of chloroacetyl chloride per mole of valine.

13. A process according to claim 12 wherein an inert gas is passed through the mixture during the reaction.

* * * * *